United States Patent
Mueller et al.

(10) Patent No.: US 6,558,927 B1
(45) Date of Patent: May 6, 2003

(54) METHOD FOR THE 5'-CAP-DEPENDENT AMPLIFICATION OF CDNAS

(75) Inventors: Manfred W. Mueller, Klosterneuburg (AT); Wolfgang M. Schmidt, Vienna (AT)

(73) Assignee: Roche Diagnostics Corporation, Indianapolis, IN (US)

( * ) Notice: Subject to any disclaimer, the term of this patent is extended or adjusted under 35 U.S.C. 154(b) by 0 days.

(21) Appl. No.: 09/566,794

(22) Filed: May 5, 2000

(51) Int. Cl.[7] .......................... C12P 19/34; C12Q 1/68; C07H 21/02; C07H 21/04
(52) U.S. Cl. ................. 435/91.1; 435/91.2; 435/6; 536/23.1; 536/24.2; 536/24.3
(58) Field of Search ......................... 435/91.1, 6, 91.2, 435/91.51; 536/23.1, 24.3, 24.2

(56) References Cited

U.S. PATENT DOCUMENTS 5,407,800 A * 4/1995 Gelfand et al. ................. 435/6

FOREIGN PATENT DOCUMENTS

WO    WO 98/48053    * 10/1998    ............ C12Q/1/68

OTHER PUBLICATIONS

Schmidt, W. M. et al., "Controlled ribonucleotide tailing of cDNA ends (CRTC) by terminal deoxynucleotidyl transferase: a new approach in PCR–mediated analysis of mRNA sequences", Nucleic Acids Research, vol. 24, pp. 1789–1791 (1996).*

* cited by examiner

Primary Examiner—Kenneth R. Horlick
Assistant Examiner—Teresa Strzelecka
(74) Attorney, Agent, or Firm—Charles M. Doyle; George C. Jen; Pennie & Edmonds, LLP

(57) ABSTRACT

The invention concerns a method for the modification, cloning and amplification of cDNAs which are complete at their 5' end which is essentially characterized in that the first strand cDNA synthesis is carried out in the presence of manganese$^{2+}$ ions or manganese$^{2+}$ is added as an additive at a later time. The CAP structure at the 5' end of the reversely transcribed mRNA triggers the attachment of deoxycytosines to the 3' end of the cDNA with high efficiency. In a preferred embodiment a controlled ribonucleotide tailing is carried out with the aid of terminal transferase following the first strand cDNA synthesis.

27 Claims, 8 Drawing Sheets

CAP / Oligo(dT)V anchor

1. FIRST-STRAND cDNA SYNTHESIS
(Reverse Transcriptase; MnCl$_2$-buffer)

2. RIBONUCLEOTIDE TAILING with rATP
(Terminal Transferase)

3. SELECTIVE LIGATION of full-length cDNA
(T4 DNA Ligase)

4. PCR AMPLIFICATION
(Taq DNA Polymerase)

mRNA primer  anchor primer

5.1 DIRECT SOLID-PHASE SEQUENCING
or
5.2 LIBRARY CONSTRUCTION

Enhanced-CRTC

5'-RACE

METHOD FOR THE 5'-CAP-DEPENDENT AMPLIFICATION OF CDNAS

The present application claims priority to co-pending German Patent Application No. 19920611.2, filed May 5, 1999, which is incorporated by reference herein in its entirety.

FIELD OF THE INVENTION

The invention originates from the field of cloning and amplification of nucleic acids and concerns a method for cloning cDNAs that are complete at the 5' end.

BACKGROUND OF THE INVENTION

The molecular analysis of messenger RNAs (mRNAs) that have been transcribed in vivo is usually carried out by generating and cloning so-called cDNAs. For this a previously isolated, poly-adenylated mRNA is firstly reversely transcribed using an oligo-dT primer i.e. it is transcribed into a single-stranded cDNA which is complementary to the mRNA. Subsequently a second strand which is complementary to the single-stranded cDNA is polymerized by methods known to a person skilled in the art to form a double-stranded cDNA. After amplifying and cloning the cDNA or parts of the cDNA using conventional molecular-biological methods (cf. Sambrook, Molecular Cloning, Laboratory Manual, 2nd edition, chapter 14), it is possible to subsequently determine the sequence of the mRNA. However, a disadvantage of this method is that it is seldom possible to identify and clone cDNAs which have a complete 5' end or can only be achieved with a very low efficiency. The reason for this is an inefficient reverse transcription reaction due to formation of intramolecular secondary structures as well as a limited amount of starting material whose RNA content is of inadequate quality. An additional disadvantage is that a loss of terminal 5' sequences of the mRNA occurs in conventional methods due to the manner in which the second strand is synthesized.

Various methods which have been developed in the past to overcome this problem have concentrated on using the cap structure of the mRNA which occurs at the 5' end of complete cDNAs as an additional selection criterion. This is a terminal guanosine residue which is methylated at position 7 and is linked by a 5'—5' bond to the actual mRNA.

In the oligo capping method (Maruyama and Sugaru, Gene 138, 171–174, 1994) the cap structure is firstly removed enzymatically by a suitable phosphatase treatment and replaced by an oligonucleotide which is linked to the 5' end of the mRNA by a suitable ligation step. However, this method requires many enzymatic steps and a large amount of poly-A-mRNA as the starting material.

Another method, the Cap Finder method (Clontech, Clontechniques 11, 1 (1996), Maleszka and Stange, Gene 202, 39–43 (1997)) is based on a marginal terminal transferase activity of the reverse transcriptase which leads to a so-called template switching effect: In a first strand cDNA synthesis a few deoxy-cytosine residues are added selectively to the 3' end of the cDNA by the reverse transcriptase under suitable conditions. This produces an anchor sequence for a so-called template switching oligonucleotide with a 3' end composed of guanosine residues which, after hybridization to the anchor sequence, serves as a primer for the second strand synthesis of the cDNA. However, the terminal transferase activity of the reverse transcriptase which apparently begins at the 7-methyl-guanosine-cap structure of the mRNA and adds the cytosine residues, has previously not been characterized in detail so that the influence of certain secondary structures of the mRNA template or of the cDNA end on the template switching activity was unknown at the time of the invention and according to the prior art the reaction could only be carried out with a low efficiency.

In an alternative method (WO 97/26368) a suitable anchor sequence is synthesized with the aid of a terminal transferase enzyme which is different from the reverse transcriptase in the process of which two to four ribonucleotides (instead of deoxyribonucleotides) are attached as an anchor sequence to the 3' end of the first strand cDNA. However, a disadvantage of this method is that the cDNA synthesis cannot be carried out selectively for 5'-cap mRNAs.

SUMMARY OF THE INVENTION

Hence the technical object of the invention was to develop an additional method for the modification, cloning or amplification of cDNAs which is used to obtain cDNAs that have a complete 5' end in the simplest possible manner and as efficiently as possible.

This technical object is achieved in that the terminal transferase reaction that elongates the first strand cDNA with deoxy-cytosines is carried out by a reverse transcriptase in the presence of magnesium$^{2+}$ ions as well as in the presence of manganese$^{2+}$ ions. The manganese concentration to be used is preferably 1–20 mM and under optimized conditions 8 mM.

In one embodiment the manganese$^{2+}$ ions can already be contained in the buffer system used during the cDNA first strand synthesis. Alternatively an incubation in the presence of manganese$^{2+}$ ions can be carried out directly after a first strand cDNA synthesis carried out in the absence of manganese$^{2+}$ ions in which case the reverse transcriptase used originally is still active under these conditions.

In this process the reverse transcriptase develops a terminal transferase activity which leads to an efficient addition of 2 to 4 deoxy-cytosine residues at the 3' terminus of the newly synthesized cDNA. This reaction is extremely efficient and also dependent on the presence of the cap structure at the 5' end of the mRNA template.

In both embodiments the deoxy-nucleotide tailing in the presence of Mn$^{2+}$ ions according to the invention not only results in a high efficiency of the tailing reaction. At the same time the specificity of the reaction is retained i.e. the addition of two to four deoxy-cytosine residues in the presence of a 5'-cap structure on the mRNA template.

Any reverse transcriptase enzymes can be used with the only restriction that the enzyme that is used should not have any RNAseH activity.

A so-called "anchor primer" is preferably used as the primer for the first strand synthesis which is composed of two parts: a so-called "anchor sequence" is located at the 5' end which can serve as a target sequence for PCR primers in amplification reactions that take place at a later time. In contrast the 3' terminal end is composed of a sequence that can hybridize with the mRNA to be identified. This can for example be an oligo-dT sequence which hybridizes with the poly-A tail 3' end of the mRNA.

Following a cDNA synthesis according to the invention, the first strand cDNA is reacted in a preferred embodiment with a ribonucleotide triphosphate or comparable derivatives such as 2'-O-methyl or 2'-O-amino nucleotide triphosphates in the presence of a terminal transferase that is different from reverse transcriptase to form an anchor sequence of ribonucleotide residues at its 3' end. When a certain ribonucleotide triphosphate is used, the reaction is referred to as controlled ribonucleotide tailing (CTRT). The ribonucleotide is preferably not CTP; the use of ATP is particularly advantageous.

The present invention also concerns methods in which the product of the reaction is subsequently linked to an additional double-stranded nucleic acid molecule which has a 3'-overhanging end that is complementary to the 3' end of the product of the reaction. Suitable additional double-stranded nucleic acid molecules are for example DNA vectors or short adaptor molecules which have target sequences for PCR primers for the subsequent amplification.

Furthermore the double-stranded nucleic acid molecules that are used can contain sequences which facilitate a subsequent analysis after the amplification is completed. These for example include promoter sequences suitable for in vitro transcription such as the prokaryotic T7, T3 or SP6 promoters and also restriction cleavage sites of which rare cleavage sites for so-called rare cutter enzymes such as NotI are particularly preferred.

The additional double-stranded nucleic acid molecule is preferably ligated to the 3' end of the product of the above mentioned reaction. In this connection it has turned out that hybridization of the adaptor to the first strand cDNA is particularly efficient in the presence of standard ligation buffers containing DMSO and efficiencies of more than 90% can be achieved. Concentrations of 5–10 vol. % DMSO have proven to be advantageous. A concentration of 7.5 vol % was determined during the optimization of the reaction.

This step includes the actual selection of full-length cDNA molecules which have the specific 3' overhangs as a result of the selection of adaptors or vectors. These overhangs are essentially characterized in that they are completely complementary to the 3' end of the initially synthesized full-length cDNA. This is accomplished by the overhang being composed of 3 or 4 deoxy-thymidine residues followed by 3 deoxy-guanosine residues when ATP is used for the terminal transferase reaction.

Due to the fact that the number of nucleotide residues added to each cDNA molecule during the tailing reaction of the reverse transcriptase and during the controlled ribonucleotide tailing is not completely identical, it has proven to be advantageous when the adaptors are composed of a mixture of molecules whose 3' overhangs vary between 3 and 4 deoxy-thymidine residues and possibly also between 3 and 4 deoxy-guanosine residues.

Consequently a mixture of double-stranded DNA adaptors containing 3' overhangs composed of 5'-dT$_{3-4}$dG$_3$-3' is also a subject matter of the invention. The invention also concerns single-stranded cDNAs which have a non-mRNA template coded 3' end composed of 5'-dC$_{3-4}$-rA$_{3-4}$-3'.

In the subsequent amplification according to the invention using PCR it is possible to distinguish between several basic methods:

A) Construction of a cDNA Gene Bank

A primer pair comprising an adaptor primer and a so-called anchor primer is used for this. As described above the adaptor primer that is used is directed against the double-stranded sequence of the DNA adaptor molecule. In contrast the sequence of the anchor primer corresponds to the anchor part that was attached to the 5' end of the cDNA during the first strand cDNA synthesis by the reverse transcriptase reaction. The pool of amplification products formed in this manner potentially contains numerous different full-length cDNAs and can be used to generate a cDNA gene bank by conventional molecular biological methods.

FIG. 1 shows a schematic overview of the method according to the invention: The method combines the 5' CAP-dependent addition of 3–4 cytosine residues to the 3' terminus of full-length first strand cDNAs by the reverse transcriptase (RT) (1., with the inventive use of a reaction buffer containing manganese chloride) with the technique of controlled ribonucleotide tailing of cDNA ends (CRTC) by the enzyme terminal transferase and rATP (2.). The terminal sequence motif (5'-dC$_3$rA$_{3-4}$) formed in this manner enables the full-length cDNA to be selectively ligated to a double-stranded DNA adaptor (5'-dT$_{3-4}$dG$_3$) using T4 DNA ligase (3.). This method leads to the specific amplification of full-length cDNAs which contain a complete 5' sequence of the mRNA. Subsequently a cDNA bank can be constructed (5.2.) after a suitable amplification by PCR.

B) Isolation and Amplification of a Specific mRNA for which Partial Sequence Information is Available.

In this step a so-called adaptor primer and an mRNA primer are used as the primers for amplification. The adaptor primer is directed against the double-stranded region of the DNA adaptor molecule. In contrast the mRNA primer is complementary to a previously known sequence section of the mRNA. The amplification products obtained in this manner represent cDNAs which are complete at their 5' end but have a sequence section of a particular length missing at their 3' end that depends on the choice of the mRNA primer.

If the mRNA to be identified is a weakly expressed species, it can be amplified again in a nested PCR using an additional primer pair of which one primer is in turn directed against the double-stranded adaptor sequence and an additional primer is directed against an internal sequence of the mRNA.

In a special embodiment the adaptor primer can contain an immobilizable label such as biotin so that the amplification products that are formed can be bound to a solid phase coated with streptavidin. In this manner the amplification products can for example be more simply analysed by direct sequencing.

The invention additionally concerns methods in which the cDNA is amplified using a primer provided with an immobilizable group. In an alternative embodiment the double-stranded DNA adaptor molecule is, by contrast, provided with an immobilizable group. As a result the amplification product, whose generation is dependent on cDNA, can be coupled to a solid phase for further analysis.

The invention additionally concerns in particular methods which are characterized in that the amplification reaction is carried out several times. This repeated amplification can be carried out with several amplification primers in the form of a nested PCR.

The invention also concerns particular embodiments of the inventive method in which the amplification product is subsequently directly sequenced.

In addition to the said methods, other amplification methods are also a subject matter of the invention which are based on special analytical formats such as differential display (WO 93/18176), serial analysis of gene expression (U.S. Pat. No. 5,695,937), subtractive hybridization (Wang et al., Proc. Natl. Acad. Sci. USA 88:11505 (1991)) or linear amplification with the aid of T7 RNA polymerase.

EXAMPLES

Example 1

5'-CAP-dependent Terminal Transferase Activity of the SuperScript™ RT

The terminal transferase activity of the SuperScript™ RT (Gibco BRL) was tested under the following conditions using an in vitro transcribed 226nt RNA (β-globin from the rabbit, GenBank V00882, fragment (pos. 633–1335) cloned in pBlueScript KS between KpnI and EcoRI, T3 transcription, termination by NcoI digestion with the plasmid) with either 5'-CAP (1; 4), 5'-phosphate (2; 5) or 5'-OH (3; 6) termini generated by standard methods.

| | | |
|---|---|---|
| 10 µl | (8 ng/µl) RNA | [89 ng] |
| 1 µl | (1 µM) oligo ($^{32}$P-labl.) | [0.05 µM each] |
| 4 µl | (5x) RT buffer | [50 mM Tris-Cl 8.3, 75 mM KCl, 3 mM MgCl$_2$] |
| 1 µl | (100 mM) DTT | [5 mM] |
| 1 µl | (20x) MnCl$_2$ buffer | [8 mM MnCl$_2$] |
| 1 µl | (10 mM) dNTPs | [0.5 mM] |
| 1 µl | (40 u/µl) RNAse inhibitor | [40 units] |
| 1 µl | (200 u/µl) SuperscriptII ™ | [200 units] |
| total volume: | 20 µl | |

A β-globin-specific 5'-terminal $^{32}$P-labelled 20mer was used as the oligonucleotide (GenBank V000882, nucleotide pos. 661–680).

Figure 1:
FIG. 1: overview scheme of the method for cap-selective CRTC.
Figure 1:
Figure 1:
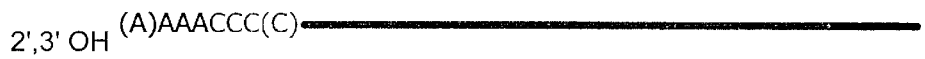
Figure 1:
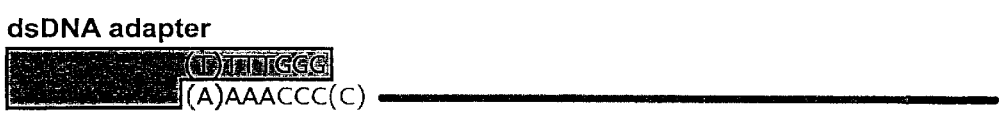
Figure 1:
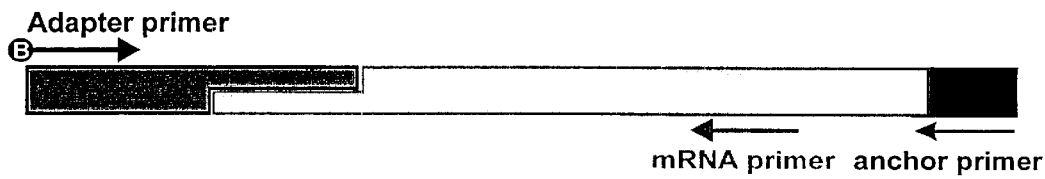
Figure 2:
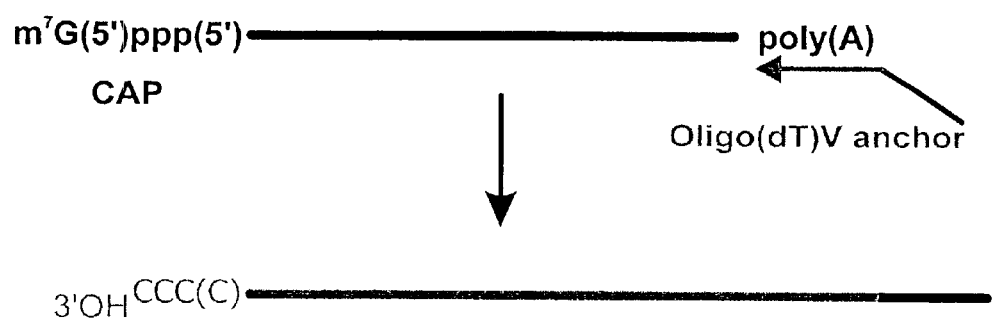
FIG. 2: first strand cDNA synthesis: 5'-CAP-dependent terminal transferase activity of a reverse transcriptase in the presence of manganese chloride.
Figure 2:
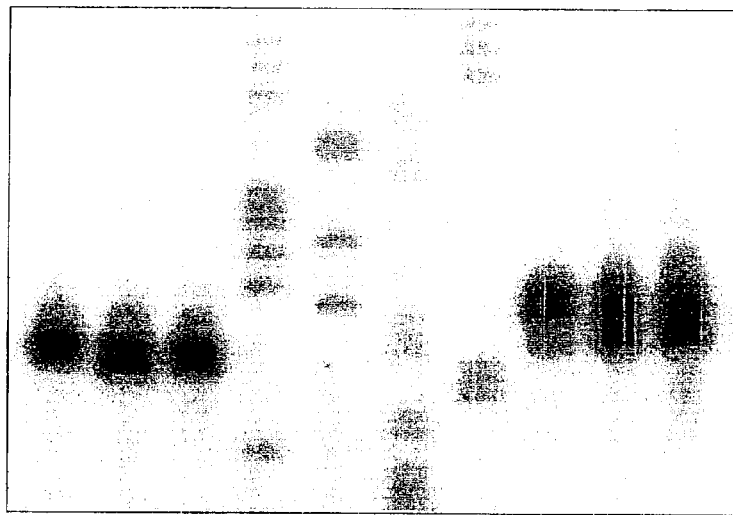

The reaction mixtures were denatured for 3 min at 80° C. and shock-cooled at 4° C. for 3 min before adding the enzyme. After adding the enzyme the mixtures were incubated for 60 min at 42° C. Subsequently the reaction products were separated on a 10% polyacrylamide/8M urea gel and quantified on a PhoshorImager. A sequence that was generated with the same oligonucleotide from a cloned fragment of a globin gene was used as a length control. The result is shown in FIG. 2. The transferase activity is limited to the addition of one nucleotide in the RT buffer without addition of manganese (1-3); the reaction occurs with a higher processivity with an mRNA template which has a 5'-CAP terminus (1, 73%+1) compared to 5'-OH (2, 57%+1) or 5'-phosphate (3, 22%+1). In contrast, when a buffer system containing manganese chloride (4-6) is used, the transferase activity of the reverse transcriptase is not only dependent on the CAP structure at the 5' terminus of the mRNA template but it is also much more efficient. The proportion of molecules with more than +2nt is 91%. In the case of 5'-CAP termini (4) it is 49% for +3nt and 42% for +4nt compared with 57% for +1nt and 39% for +3nt in the case of 5'-phosphate (5) and 40% for +1nt, 22% for +2nt and 34%+3nt in the case of 5'-OH termini (6).

Alternatively manganese chloride at a final concentration of 10 mM was not added until after the cDNA synthesis before the reaction mixtures were incubated for a further 10 min. No significant differences with regard to the efficiency of the tailing reaction were found compared to adding manganese chloride at the beginning of the reaction.

Example 2

5-CAP-dependent Terminal Transferase Activity: Comparison of Various RTs

Figure 3:
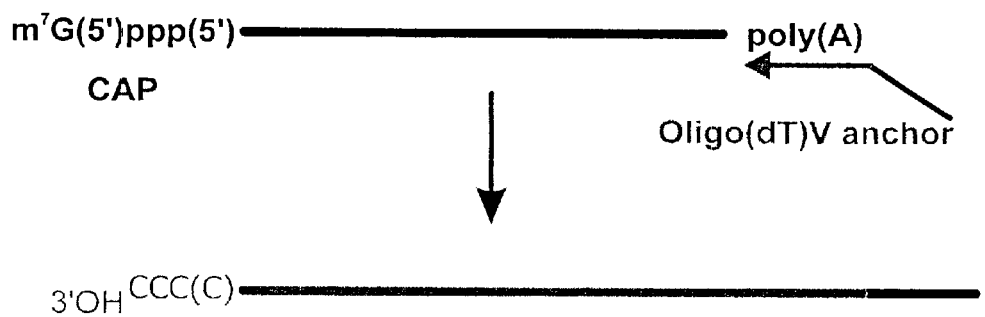
FIG. 3: 5'-CAP-dependent terminal transferase activity with various reverse transcriptases.
Figure 3:
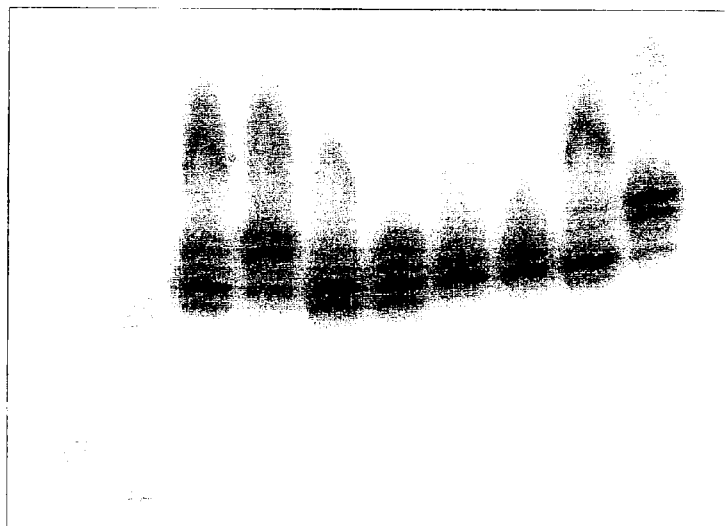

The experiment described in Example 1 was repeated with various reverse transcriptase enzymes. The result is shown in FIG. 3. RTs with and without RNaseH activity [Mu-MLV (3,4) and AMV (5,6) and Expand™ RT (1,2) and SuperScript™ (7,8)] were compared with regard to terminal transferase activity during cDNA synthesis using a 5'-CAP mRNA template. For this the respective reaction buffer of the manufacture was either tested in its original form (1,3, 5,7) or containing 8 mM manganese chloride as an additive (2,4,6,8). A manganese chloride dependent transferase activity was only found in the case of the RNaseH-deficient enzymes. In this connection SuperScript™ and Expand™ RT only differed slightly with regard to the efficiency of the incorporation of 3 or 4 cytosine residues (Expand™ RT (2): +3: 43%, +4: 31%; SuperScript™ (8): +3: 8%, +4: 81%).

Example 3

Terminal Transferase Activity of the Expand™ RT: Manganese Dependency

Figure 4:
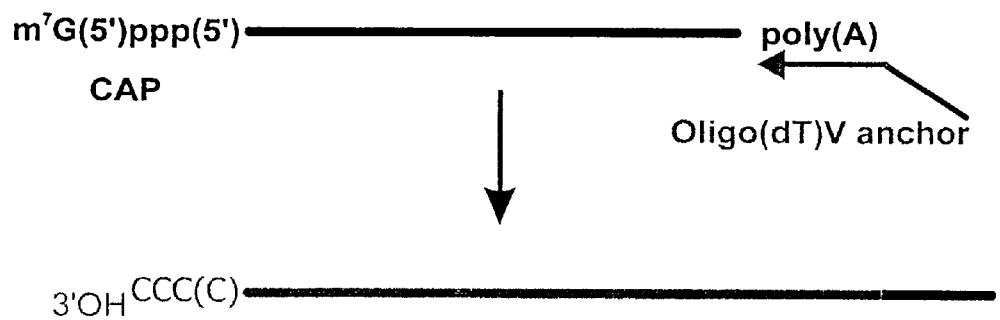
FIG. 4: manganese-dependency of the terminal transferase activity of reverse transcriptase.
Figure 4:
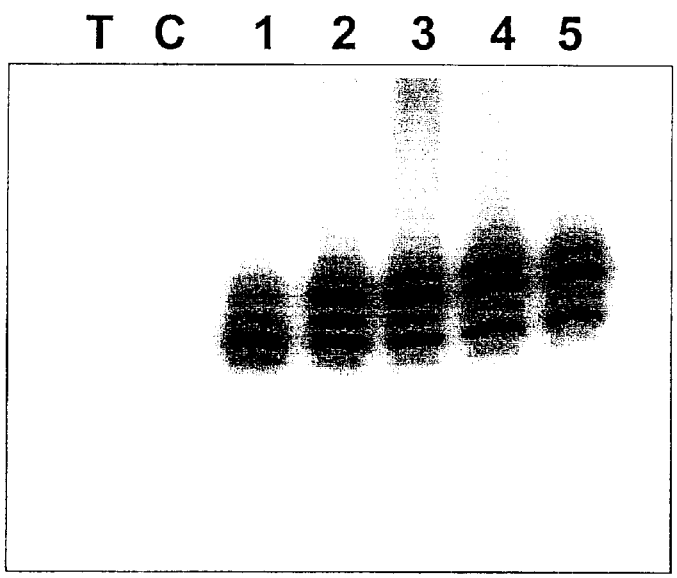

The experiment described in Example 1 was repeated as shown in FIG. 4 with the Expand reverse transcriptase™ (Roche Molecular Biochemicals) and various manganese chloride concentrations (0 mM (1), 2 mM (2), 4 mM (3), 8 mM (4), 10 mM in an additional 15 min incubation after the cDNA synthesis (5)). The following efficiencies with regard to the incorporation of a 3rd and 4th nucleotide were determined: 23% (0 mM), 43% (2 mM), 63% (4 mM), 73% (8 mM), 70% (10 mM, post incubation).

Example 4 rATP-Tailing with Terminal Transferase (ribotailing

After a suitable purification (Roche Molecular Biochemicals High pure Purification Kit) the cDNA synthesized according to the invention from Example 1 was incubated in the following reaction mixture for 30 min at 37° C.:

| | | |
|---|---|---|
| 20 µl | cDNA | |
| 6 µl | (5 x) TdT buffer | [200 mM K-cacodylate, 25 mM Tris-Cl 6.6, 0.25 mg/ml BSA] |
| 3 µl | (25 mM) CoCl$_2$ | [2.5 mM] |
| 0.5 µl | (10 mM) ATP | [167 µM] |
| 0.5 µl | (25 U/µl) terminal transferase | [12.5 units] |
| total volume: | 30 µl | |

Figure 5:
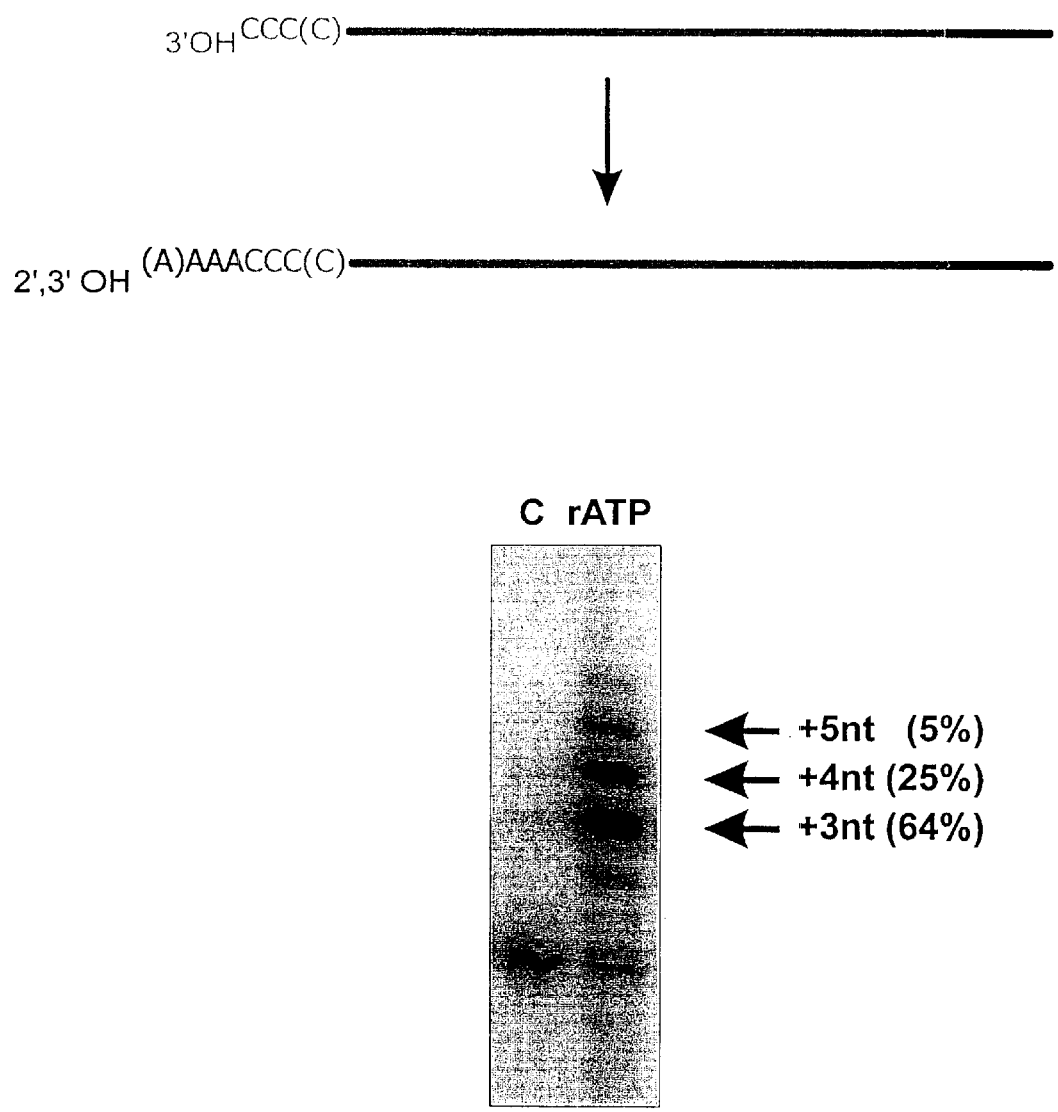
FIG. 5: controlled ribonucleotide tailing with rATP.

In order to analyse the efficiency of the reaction the experiment was repeated with a $^{32}$P-labelled deoxy-oligonucleotide (20 mer) instead of cDNA under the same reaction conditions. The result is shown in FIG. 5: The reaction products were separated on a 20% polyacrylamide/8 M urea gel and quantified on a PhosphorImager. A total reaction efficiency of 94% was determined with regard to the addition of 3 (64%), 4 (25%) or 5 (5%) adenosine residues.

Example 5

Selective Ligation to the Adaptor

After a standard ethanol precipitation the cDNA which was previously treated with terminal transferase was resuspended in 15 µl water and ligated with a population of adaptor molecules: The adaptors were composed of a double-stranded region of 50 base pairs with a 6–7 nucleotide 3' overhang of [5'-$T_{3-4}G_3$-3']. The ligation mixture was composed as follows:

| | | | |
|---|---|---|---|
| 13 µl | | ATP-tailed cDNA | |
| 2 µl | (50 ng/µl) | 56/57 bp adaptor | [100 ng, 3 pmol] |
| 2 µl | (10 x) | ligation buffer | [66 mM Tris-Cl 7.5, 5 mM $MgCl_2$, 1 mM DTT, 1 mM ATP] |
| 1.5 µl | | DMSO | [7.5 vol %] |
| 1.5 µl | (1 u/µl) | T4 DNA ligase | [1.5 units] |
| total volume: | 20 µl | | |

After incubation for 5 min at 37° C. and 2 min at 24° C. to selectively hybridize the adaptor overhang to the 3'-tailed end of the cDNA, the mixture was incubated for 16 h at 16° C. for ligation.

Figure 6:
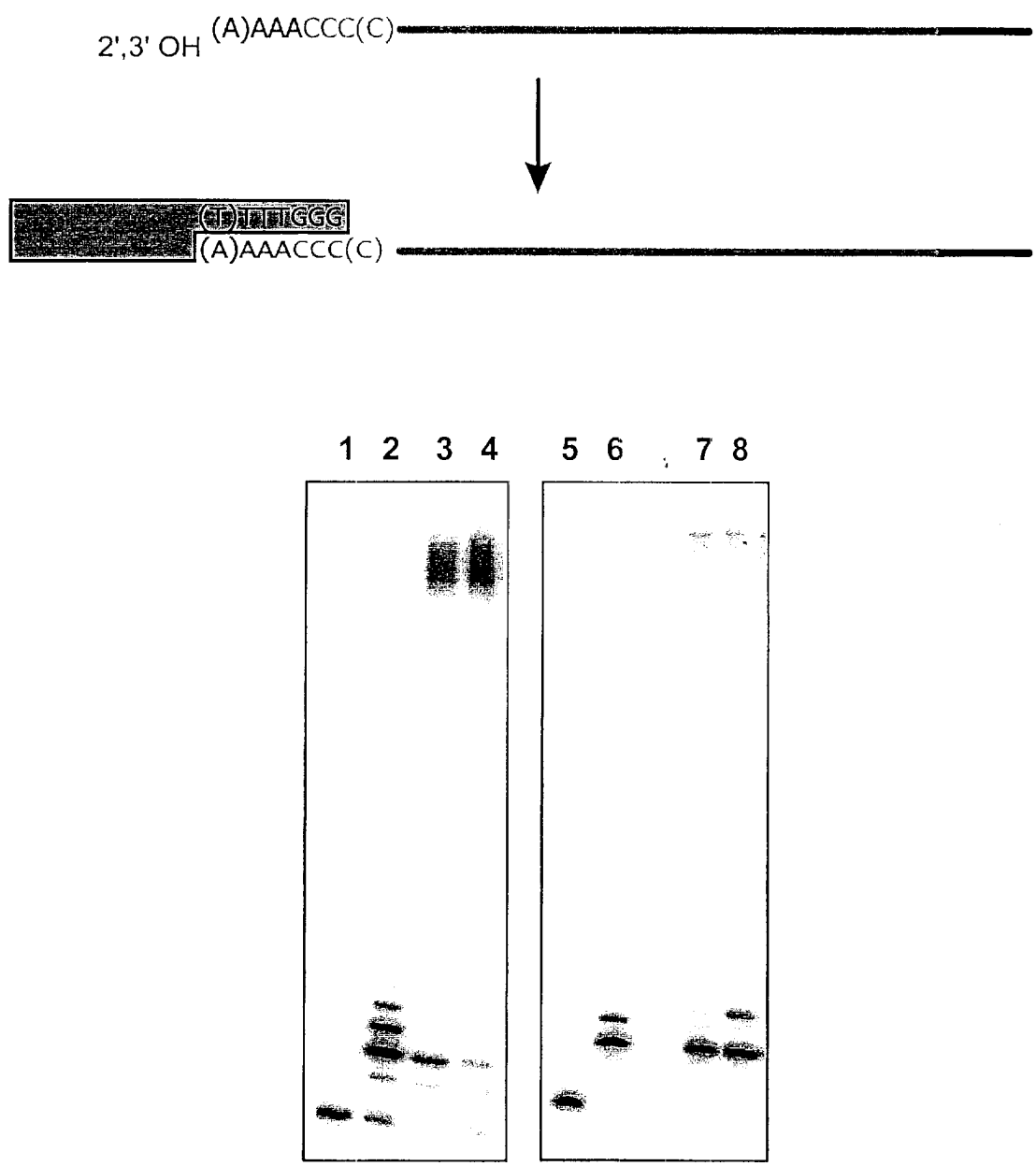
FIG. 6: selective ligation of full-length cDNA.

The selectivity of the ligation to the adaptor was also tested in an assay using $^{32}$P-labelled oligonucleotide (20 mer). The result is shown in FIG. 6. Oligonucleotides with compatible (3'-CCC, 1-4) and incompatible (3'-AGC, 5-8) 3'-termini were compared. The oligonucleotides (1 or 5) were ligated to the adaptor [5'-$G_3T_{3-4}$] after rATP tailing as described in Example 4 (1 or 6) in a standard ligation mixture containing T4 DNA ligase (3 or 7) or DMSO (7.5% v/v) as an additive (4 or 8). The reaction products were separated in a 15% polyacrylamide/8 M urea gel and quantified on a PhosphorImager. The result of adding DMSO (4) is that 93% (compared to 77% under standard conditions, 3) of the cDNA fraction is ligated with compatible 3'-termini. Furthermore the ligation conditions are selective i.e. even molecules which are terminated by a C are only ligated under these conditions by 14% (7) or 8% (8) using DMSO in the buffer. This results in an increase in the selective isolation of complete cDNAs.

Example 6

Amplification of a Human GAPDH-cDNA Produced and Modified According to the Invention Compared to Amplification by 5'-RACE Starting with various amounts of a poly-A+ mRNA (10 ng, 2.5 ng, 0.5 ng, 100 pg, 20 pg) isolated from the human cell line MOLT-3 (ATCC strain collection No. CRL-1552), a cDNA synthesis according to the invention was carried out according to Examples 1, 4 and 5 using deoxy-cytosine tailing, a terminal transferase reaction with rATP and a ligation with an adaptor according to the invention.

Subsequently a PCR reaction was carried out under the following conditions for the specific amp of GAPDH (glyceraldehyde-3-phosphate dehydrogenase):

| | | | |
|---|---|---|---|
| 2 µl | | aliquot of the ligation from example 5 | |
| 1 µl | (50 µM) | primer STI-2 | [1 µM]; |
| 1 µl | (50 µM) | primer GAPDH-2/M | [1 µmM] |
| 1 µl | (10 mM) | dNTPs | [0.5 mM] |
| 5 µl | (10x) | Expand ™ buffer | [Roche Molecular Biochemicals, containing 1.5 mM $Mg^{++}$] |
| 39.5 µl | | $H_2O$ | |
| 0.5 µl | (3.5 u/µl) | Expand ™ | [Roche Molecular Biochemicals] |
| total volume: | 50 µl | | |

| thermocycles: | | | |
|---|---|---|---|
| | 1 x | 30 sec | 72° C. |
| | 1 x | 3 min | 94° C. |
| | 35 x | 20 sec | 94° C. |
| | | 30 sec | 64° C. |
| | | 40 sec | 72° C. |
| | 1 x | 5 min | 72° C. |

GAPDH-2M is a 24mer corresponding to nucleotide position 83–106 from exon 4 (GenBank acc. No. J04038) of the GAPDH gene with a calculated melting point Tm of ca. 70° C. The STI-2 primer had a length of 20 deoxy nucleotides and a calculated melting point Tm of ca. 69° C. GAPDH was amplified in parallel mixtures using the same amplification primers and the amplification protocol of the 5' RACE method known from the prior art (Frohmann, M. (1994) PCR Methods and Applications, 4,540–558).

Figure 7:
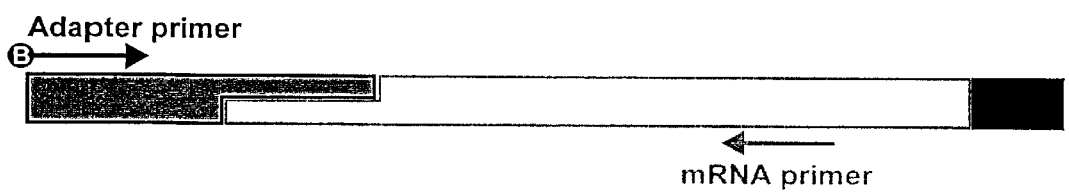
FIG. 7: inventive amplification with the aid of PCR.
Figure 7:
Figure 7:
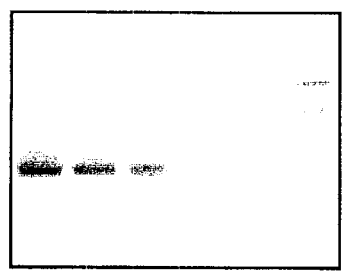
Figure 7:
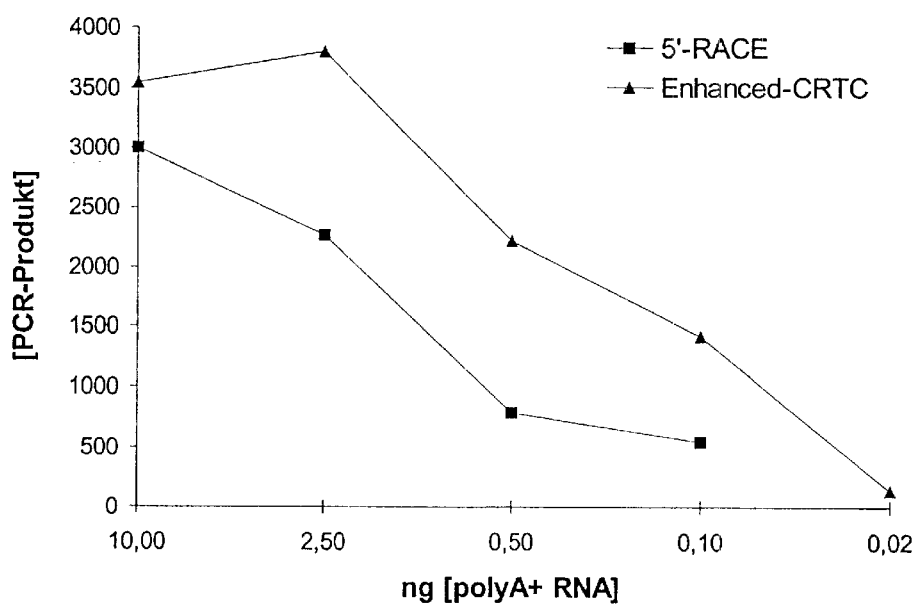

The PCR products were separated in a 1.25% agarose gel and evaluated by densitometry. The result shown in FIG. 7 demonstrates that the sensitivity of the method according to the invention is considerably higher than the 5' RACE method of the prior art.

Example 7

Direct Sequencing of the PCR Amplificate by Enhanced CRTC

Figure 8:
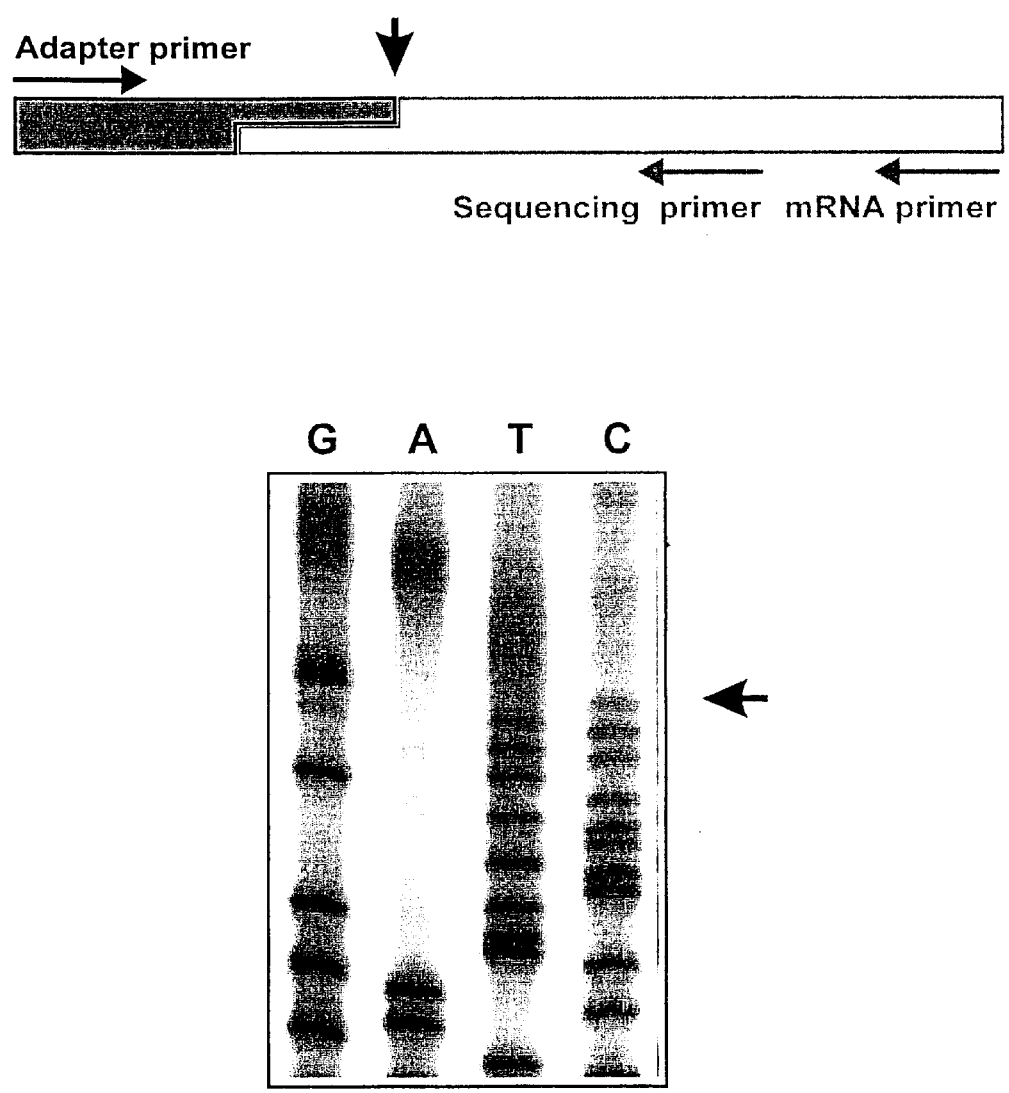
FIG. 8: direct sequencing of inventive amplified cDNA.

The amplification product obtained according to the invention from Example 6 was sequenced according to the principle of the dideoxy method as described in Schmitt and Müller, Nucl. Acids Res. 24, 1789–1791 (1996) using an IRD800 fluorescent-labelled GAPDH primer corresponding to nucleotide position 78 to 97 from exon 3 of the GAPDH gene (GenBank acc. No. J04038, Ercolani L., Florence B., Denaro M., Alexander M.; Isolation and complete sequence of a functional human glyceraldehyde-3-phosphate dehydrogenase gene; J. Biol. Chem. 263: 15335–15341 (1988)) in the direction of the transcription start. As shown in FIG. 8 the sequence allows the exact allocation of the transcription start (arrow) of the human GAPDH gene.

The present invention is not to be limited in scope by the exemplified embodiments which are intended as illustrations of single aspects of the invention. Various modifications of the invention in addition to those described herein will become apparent to those skilled in the art from the foregoing description and accompanying drawings. Such modifications are intended to fall within the scope of the appended claims. All publications cited herein are incorporated by reference in their entirety.

What is claimed is:

1. A method for the synthesis of a cDNA, comprising incubating an mRNA with a primer and reverse transcriptase in the presence of magnesium$^{2+}$ ions and manganese$^{2+}$ ions and synthesizing a strand of cDNA, wherein the concentration of manganese$^{2+}$ ions is at least 1 mM but at most 20 mM during the cDNA synthesis.

2. The method of claim 1, wherein after the cDNA synthesis, the cDNA is reacted with a ribonucleotide triphosphate or a modified nucleotide triphosphate in the presence of terminal transferase forming a 3' anchored cDNA.

3. The method of claim 2, wherein the 3' anchored cDNA is linked to a double stranded DNA adapter with a 3' over-hanging end complementary to the 3' end of the 3' anchored cDNA forming a 3' anchored cDNA/double stranded DNA adapter complex.

4. The method of claim 3, wherein the double stranded DNA adapter is a vector or an adaptor molecule.

5. The method of claim 3, wherein the double stranded DNA adapter is ligated to the 3' end of the 3' anchored cDNA.

6. The method of claim 5, wherein the ligation is carried out in the presence of 5 to 10 vol % DMSO.

7. The method of claim 6, wherein the ligation is carried out with an efficiency of about 90% to about 93%.

8. The method of claim 5, wherein the 3' anchored cDNA is amplified using a primer linked to an immobilizable group.

9. The method of claim 4, wherein the double stranded DNA adapter is linked to an immobilizable group.

10. The method of claim 8, wherein the 3' anchored cDNA is amplified several times.

11. The method of claim 8, wherein the 3' anchored cDNA is amplified with a first primer capable of hybridizing to the double stranded DNA adapter and second primer capable of hybridizing to the 5' end of 3' anchored cDNA, forming a first amplification product.

12. The method of claim 10, wherein amplified 3' anchored cDNA is directly sequenced.

13. A mixture of double-stranded DNA adaptors comprising 3' overhangs of 5'-dT$_{3-4}$dG$_3$-3'.

14. A first strand cDNA comprising a non mRNA template-coded 3' end of 5'-dC$_{3-4}$rA$_{3-4}$3'.

15. The method of claim 1, wherein the reverse transcriptase lacks RNAseH activity.

16. The method of claim 1, wherein the mRNA contains a cap structure at its 5'end.

17. The method of claim 11, wherein the first amplification product is further amplified with a primer capable of hybridizing to an internal sequence of the cDNA.

18. The method of claim 3, wherein the 3' anchored cDNA is amplified.

19. The method of claim 18, wherein the 3' anchored cDNA is amplified with a first primer capable of hybridizing to the double stranded DNA adapter and second primer capable of hybridizing to the 5' end of 3' anchored cDNA, forming a first amplification product.

20. The method of claim 19, wherein the first amplification product is further amplified with a primer capable of hybridizing to an internal sequence of the cDNA.

21. A method for synthesizing 3' anchored cDNA comprising:
   a) contacting mRNA with a primer and reverse transcriptase in the presence of magnesium$^{2+}$ ions and manganese$^{2+}$ ions and synthesizing first strand tailed cDNA; and
   b) contacting said first strand tailed EDNA with ribonucleotide triphosphate or a modified nucleotide triphosphate in the presence of terminal transferase forming 3' anchored cDNA.

22. A method for synthesizing 3' anchored cDNA comprising:
   a) contacting mRNA with a primer and reverse transcriptase in the absence of manganese$^{2+}$ ions and synthesizing first strand cDNA;
   b) contacting said first strand cDNA with manganese$^{2+}$ ions synthesizing first strand tailed cDNA; and
   c) contacting said first strand tailed cDNA with ribonucleotide triphosphate or a modified nucleotide triphosphate in the presence of terminal transferase forming 3' anchored cDNA.

23. The method of claim 21 or 22, wherein the reverse transcriptase lacks RNAseH activity.

24. The method of claim 21 or 22, wherein the mRNA contains a cap structure at its 5' end.

25. The-method of claim 21 or 22, wherein the 3' anchored cDNA is linked to a double stranded DNA adapter with a 3' over-hanging end complementary to the 3' end of the 3' anchored cDNA forming a 3' anchored cDNA/double stranded DNA adapter complex.

26. The method of claim 21 or 22, wherein the double stranded DNA adapter is a vector or an adaptor molecule.

27. The method of claim 21 or 22, wherein the double stranded DNA adapter is ligated to the 3' end of the 3' anchored cDNA.

* * * * *